United States Patent
Jen et al.

[11] Patent Number: 5,989,952
[45] Date of Patent: Nov. 23, 1999

[54] METHOD FOR FABRICATING A CROWN-TYPE CAPACITOR OF A DRAM CELL

[75] Inventors: Tean-Sen Jen, Chiayih; Shiou-Yu Wang, Taipei; Jia-Shyong Cheng, Hsinchu Hsien; Chi-Hui Lin, Taipei, all of Taiwan

[73] Assignee: Nanya Technology Corporation, Taiwan

[21] Appl. No.: 08/934,617

[22] Filed: Sep. 22, 1997

[30] Foreign Application Priority Data

Jun. 24, 1997 [TW] Taiwan ................... 86108834

[51] Int. Cl.$^6$ ............................. H01L 12/8242
[52] U.S. Cl. .................. 438/253; 438/255; 438/745
[58] Field of Search ................... 438/745, 253, 438/254, 255

[56] References Cited

U.S. PATENT DOCUMENTS

| | | | |
|---|---|---|---|
| 5,543,345 | 8/1996 | Liaw et al. | 438/397 |
| 5,700,731 | 12/1997 | Lin et al. | 438/381 |
| 5,792,689 | 8/1998 | Yang et al. | 438/253 |

*Primary Examiner*—Benjamin Utech
*Assistant Examiner*—Lynette T. Umez-Eronini
*Attorney, Agent, or Firm*—Michael D. Bednarek; Crowell & Moring LLP

[57] ABSTRACT

A method for fabricating a DRAM cell having a crown-type capacitor over a semiconductor substrate is disclosed. The method includes steps of: (a) forming a transistor over the semiconductor substrate; (b) forming an insulating layer over the transistor; (c) selectively etching the insulating layer to form a contact opening; (d) forming a first conducting layer over the insulating layer and filling into the contact opening; (e) forming an etching stop layer and a mask layer over the first conducting layer; (f) pattering the mask layer to form a plurality of openings; (g) forming a dielectric spacer on the sidewall of the mask layer, and removing exposed portions of the etching stop layer; (h) anisotropically etching the mask layer and the first conducting layer by using the dielectric spacer as a mask, to expose, respectively, the etching stop layer and the insulating layer; (i) removing uncovered etching stop layer to expose the first conducting layer; (j) anisotropically etching the first conducting layer to a predetermined depth by using the dielectric spacer as a mask, thereby forming a crown-type storage electrode; (k) removing the dielectric spacer and the etching stop layer; (l) forming a dielectric layer over exposed portions of the storage electrode; and (m) forming a second conducting layer as an opposite electrode over the dielectric layer.

21 Claims, 7 Drawing Sheets

METHOD FOR FABRICATING A CROWN-TYPE CAPACITOR OF A DRAM CELL

BACKGROUND OF THE INVENTION

1. Field of the Invention

The present invention relates to a method for fabricating a semiconductor memory device, and more specifically, to a method for fabricating a crown-type capacitor of a dynamic random access memory (DRAM) cell, thereby improving the uniformity of a spacer in the capacitor structure, and providing a larger process window.

2. Description of Related Art

A conventional DRAM cell, referring to FIG. 1, consists of a transistor T and a capacitor C. The source of the transistor T is connected to a corresponding bit line BL. The drain of the transistor T is connected to a storage electrode of the capacitor C. The gate of the transistor is connected to a corresponding word line WL. An opposite electrode of the capacitor C is biased with a constant voltage source. A dielectric layer is arranged between the storage electrode and the opposite electrode. As known to those skilled in the art, the storage capacitor C is provided for data storage. Therefore, a large capacitance is required for the capacitor to prevent data loss and to lower the refresh rate.

For a conventional DRAM of less than 1 MB capacity, a two-dimensional capacitor structure is utilized for data storage. This capacitor structure is well known as a planar-type capacitor. However, in order to provide a capacitance large enough for data storage, the planar-type capacitor occupies a very large base area. This structure cannot therefore be applied in a high-density DRAM process.

Accordingly, some three-dimensional capacitor structures, such as a trench-type or stack-type structure, have been developed to satisfy the requirement of a high-integrated DRAM device of more than 16 MB. However, the trench-type structure has, evidently, defects in the substrate during the trench formation, thereby increasing leakage current and affecting the device performance. Moreover, since the etching rate of the trench decreases as the aspect ratio increases, the process becomes more difficult, and the DRAM productivity is reduced. Therefore, the trench-type structure is not that applicable in reality. The stack-type capacitor, on the contrary, is free of all the problems mentioned above. It is therefore very popular in small-dimensional memory fabrication, and has attracted a lot of attention regarding structure optimization.

Among all kinds of stack-type capacitors, a crown-type capacitor in which an electrode has an upward extending portion to provide a very large area for data storage is favorable for highly-integrated memory devices, especially for those have a capacity of more than 64 MB. The upward extending electrode can be fabricated by, for example, anisotropically etching a conducting polysilicon layer through a spacer mask. This electrode is a storage electrode. As a crown-type capacitor of a DRAM cell, the capacitor further includes a dielectric layer over the storage electrode, and an opposite electrode over the dielectric layer.

However, the steps to fabricate a crown-type capacitor are numerous and complicated, thereby affecting the DRAM productivity. Even though some process modification has simplified the steps, the process conditions have become correspondingly stricter, and are not applicable in DRAM production.

The conventional process steps of a crown-type capacitor for a DRAM cell will be described in accompaniment with the drawings of FIG. 2A through FIG. 2C. Referring to FIG. 2A, a field oxide layer 12 is formed over a semiconductor substrate 10, which is, for example, a silicon substrate, to define an active region thereon. Then a gate oxide layer 13, a polysilicon layer 14, a tungsten silicide (WSi$_x$) 15, and an insulating layer 16 are successively formed over the active region, and are etched to be a gate electrode G. By using the gate electrode G as a mask, impurities are implanted into the semiconductor substrate 10 to form lightly-doped source/drain regions 17a and 17b. A spacer 18 is formed on the sidewall on the gate structure G by depositing a dielectric layer and etching back the dielectric layer. Then the gate structure G and the spacer 18 are both utilized as a mask for further implanting impurities into the semiconductor substrate 10 to form heavily-doped source/drain regions 19a and 19b, thereby forming a transistor.

The transistor is successively covered by a first planar layer 20 and a second planar layer 21 which are both etched to form a contact window (not shown in the figure), by micro-lithography and etching, to expose the drain region 19b of the transistor. Then a first conducting layer is formed over the first planar layer 20 to fill the contact window, thereby electrically connecting the drain region 19b. This conducting layer is patterned to be a bit line of the memory device. Then a BPSG layer 22 is deposited over the first planar layer 20 and the exposed bit line surface. A contact opening is then formed through the first planar layer 20, the second planar layer 21 and the BPSG layer 22 by microlithography and etching, to expose the source region 19a as a contact region. A conducting layer 24, such as a doped polysilicon layer, is deposited over the BPSG layer 22 and fills in the contact opening 23, thereby electrically contacting the contact region.

The micro-lithography and etching steps are successively carried out to form several shallow trenches on the conducting layer 24, thereby separating several memory cell regions, that is, regions between the contact openings 23. Then a dielectric layer is deposited and etched back to form dielectric spacers 30 on the sidewalls of the shallow trenches 26.

The critical step for forming the crown-type capacitor will be described in accompaniment with the schematic diagram of FIG. 2B. Referring to FIG. 2B, using the dielectric spacers 30 as a mask, the conducting layer 24 is anisotropically etched by, for example, the reactive ion etching (RIE) method to remove the portions under the shallow trenches 26, thereby defining the capacitor regions. Since the remaining conducting layer 24 has a constant thickness of t1, a storage electrode 24 having the crown-type structure 24a is formed.

Referring to FIG. 2C, the dielectric spacers 30 are then removed. The storage electrode 24 is successively covered by a dielectric layer 27 and an opposite electrode 28, thereby forming a capacitor. The complete DRAM cell further includes a passivation layer 29 over the capacitor.

The aforementioned fabrication method utilizes the dielectric spacer 30 as a mask for anisotropically etching the conducting layer, thereby forming the crown-type structure and defining the capacitor region. Therefore, the etching condition must be precisely controlled. In order to isolate each capacitor, over etching the conducting layer is generally required, therefore reducing the conductivity due to an insufficient thickness of t1. Moreover, the crown-type structure may be broken, thereby affecting the performance of the device. Furthermore, since the crown-type structure is defined by the spacers 30, the shape of the spacers 30 transfers to the electrode structure, and a sharp-point discharge will happen to the device.

SUMMARY OF TE INVENTION

Accordingly, the present invention provides a method for fabricating a DRAM cell in which the area occupied by the storage capacitor is small but the capacitance is large enough for data storage.

The method of the invention simplifies the fabrication steps without degrading the operating parameters.

The method of the invention utilizes an amorphous silicon etch-stop layer to define the capacitor regions and, in another step, to form the crown-type structure. Through the two-step process, the fabrication method provides a wider operating scope and the uniformity of the spacer thickness is improved.

The method of the invention fabricates a DRAM cell with a crown-type capacitor over a semiconductor substrate. The method includes steps of: (a) forming a transistor including a gate, a drain and a source over the semiconductor substrate; (b) forming an insulating layer over the transistor; (c) selectively etching the insulating layer to form a contact opening in which either the source or the drain of the transistor is exposed as a contact region; (d) forming a first conducting layer over the insulating layer and filling into the contact opening to electrically connect the contact regions; (e) successively forming an etching stop layer and a mask layer over the first conducting layer, wherein the etching stop layer and the first conducting layer consist of different materials; (f) pattering the mask layer to form a plurality of openings in which regions for separating different memory cells are exposed; (g) forming a dielectric spacer on the sidewall of the mask layer, and removing exposed portions of the etching stop layer; (h) anisotropically etching the mask layer and the first conducting layer by using the dielectric spacer as a mask, to expose, respectively, the etching stop layer and the insulating layer, for defining a capacitor region; (i) removing uncovered etching stop layer to expose the first conducting layer; (j) anisotropically etching the first conducting layer to a predetermined depth by using the dielectric spacer as a mask, thereby forming a crown-type storage electrode; (k) removing the dielectric spacer and the etching stop layer; (l) forming a dielectric layer over exposed portions of the storage electrode; and (m) forming a second conducting layer as an opposite electrode over the dielectric layer.

Another method of the invention includes the steps of: (a) forming a transistor including a gate, a drain and a source over a semiconductor substrate; (b) forming an insulating layer over the transistor; (c) selectively etching the insulating layer to form a contact opening in which one source and drain of the transistor is exposed as a contact region; (d) forming a first conducting layer over the insulating layer and filling into the contact opening to electrically connect the contact region; (e) successively forming an etching stop layer and a photoresist layer over the first conducting layer; (f) patterning the photoresist layer to form a plurality of openings in which regions for separating different memory cells are exposed; (g) forming dielectric spacers on the sidewall of the photoresist layer, and removing exposed portions of the etching stop layer; (h) anisotropically etching the first conducting layer by using the dielectric spacer and the photoresist layer as a mask to expose the insulating layer for defining a capacitor region; (i) removing the uncovered etching stop layer to expose the first conducting layer; (j) anisotropically etching the first conducting layer to a pre- determined depth by using the dielectric spacer as a mask, thereby forming a crown-type storage electrode; (k) removing the dielectric spacer and the etching stop layer; (l) forming a dielectric layer over exposed portions of the storage electrode; and (m) forming a second conducting layer as an opposite electrode over the dielectric layer.

Further another method of the invention includes the steps of: (a) forming a transistor including a gate, a drain and a source over the semiconductor substrate; (b) forming an insulating layer over the transistor; (c) selectively etching the insulating layer to form a contact opening in which either the source or the drain of the transistor is exposed as a contact region; (d) forming a Ti/TiN layer covering the sidewall and bottom of the contact opening, and extending over the insulating layer; (e) forming a tungsten plug in the contact opening; (f) forming a first conducting layer over the exposed Ti/TiN surface, and electrically connecting the tungsten plug; (g) successively forming an etching stop layer and a mask layer over the first conducting layer, wherein the etching stop layer and the first conducting layer consist of different materials; (h) patterning the mask layer to form a plurality of openings in which regions for separating different memory cells are exposed; (i) forming a dielectric spacer on the sidewall of the mask layer, and removing exposed portions of the etching stop layer; (j) anisotropically etching the mask layer and the first conducting layer by using the dielectric spacer as a mask, to expose, respectively, the etching stop layer and the Ti/TiN layer, for defining a capacitor region; (k) removing the uncovered Ti/TiN layer and uncovered etching stop layer to expose the first conducting layer; (l) anisotropically etching the first conducting layer to a predetermined depth by using the dielectric spacer as a mask, thereby forming a crown-type storage electrode including the tungsten plug, the Ti/TiN layer and the first conducting layer; (m) removing the dielectric spacer and the etching stop layer; (n) forming a dielectric layer over exposed portions of the storage electrode; and (o) forming a second conducting layer as an opposite electrode over the dielectric layer.

Further another method of the invention includes the steps of: (a) forming a transistor including a gate, a drain and a source over the semiconductor substrate; (b) forming an insulating layer over the transistor; (c) selectively etching the insulating layer to form a contact opening in which either the source or the drain of the transistor is exposed as a contact region; (d) forming a first Ti/TiN layer covering the sidewall and bottom of the contact opening, and extending over the insulating layer; (e) forming a tungsten plug in the contact opening; (f) forming a second Ti/TiN layer covering the tungsten plug and the first Ti/TiN layer, wherein the second Ti/TiN layer has a thickness greater than that of the first Ti/TiN layer; (g) forming a first conducting layer over the exposed second Ti/TiN surface, and electrically connecting the tungsten plug; (h) successively forming an etching stop layer and a mask layer over the first conducting layer, wherein the etching stop layer and the first conducting layer consist of different materials; (i) patterning the mask layer to form a plurality of opening in which regions for separating different memory cells are exposed; (j) forming a dielectric spacer on the sidewall of the mask layer, and removing exposed portions of the etching stop layer; (k) anisotropically etching the mask layer and the first conducting layer by using the dielectric spacer as a mask, to expose, respectively, the etching stop layer and the Ti/TiN layer, for defining a capacitor region; (l) removing the uncovered first and second Ti/TiN layers and the uncovered etching stop layer to expose the first conducting layer; (m) anisotropically etching the first conducting layer to the second Ti/TiN layer by using the dielectric spacer as a mask, thereby forming a crown-type storage electrode including the tungsten plug, the first Ti/TiN layer, the second Ti/TiN layer and the first conducting layer; (n) removing the dielectric spacer and the etching stop layer; (o) forming a dielectric layer over exposed portions of the storage electrode; and (p) forming a second conducting layer as an opposite electrode over the dielectric layer.

In the aforementioned methods of the invention, a plurality of hemispherical silicon grain (HSG) or rugged polysilicon structures can be formed over the exposed storage electrode before the formation of the dielectric layer, thereby increasing the electrode area.

DETAILED DESCRIPTION OF THE INVENTION

Embodiment 1

Figure 1:
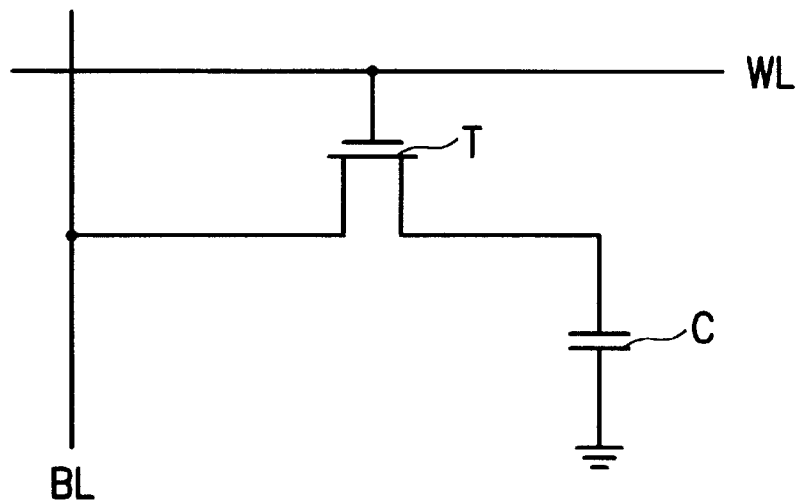
FIG. 1 is a schematic diagram illustrating a conventional DRAM cell.
Figure 2A:
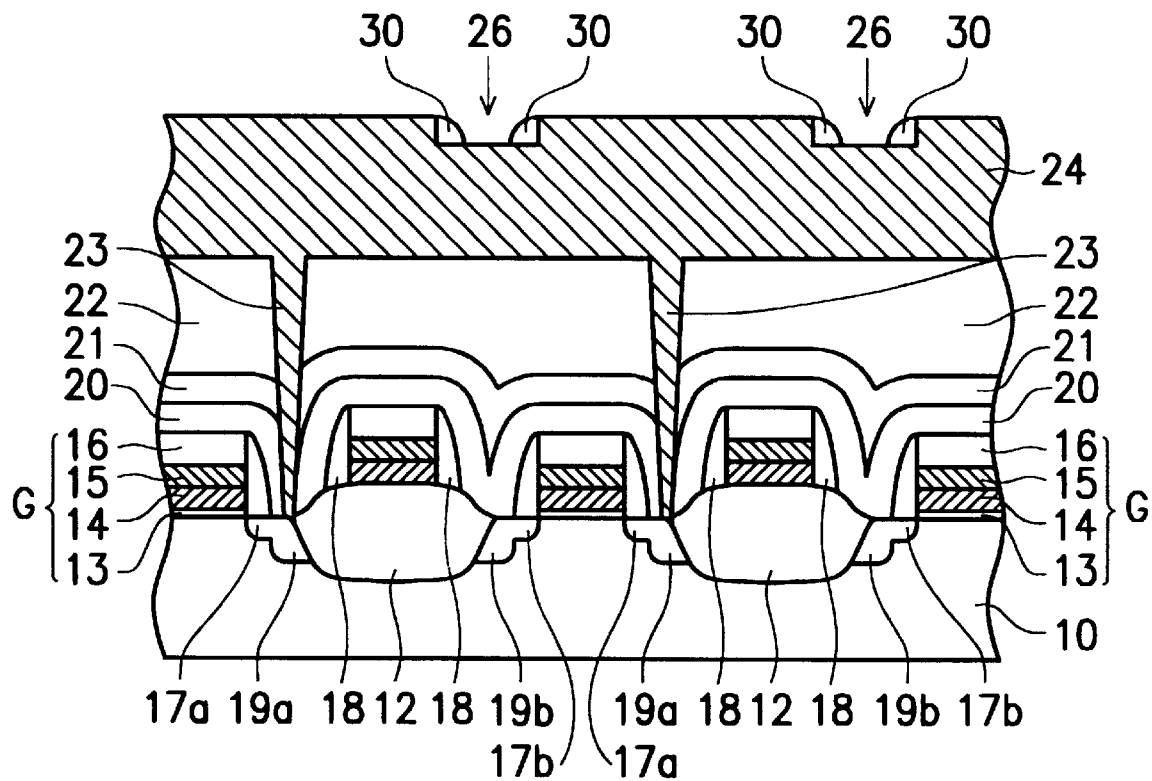
FIG. 2A, 2B, 2C are cross-sectional views illustrating the fabrication steps of a conventional DRAM cell having a crown-type capacitor.
Figure 2B:
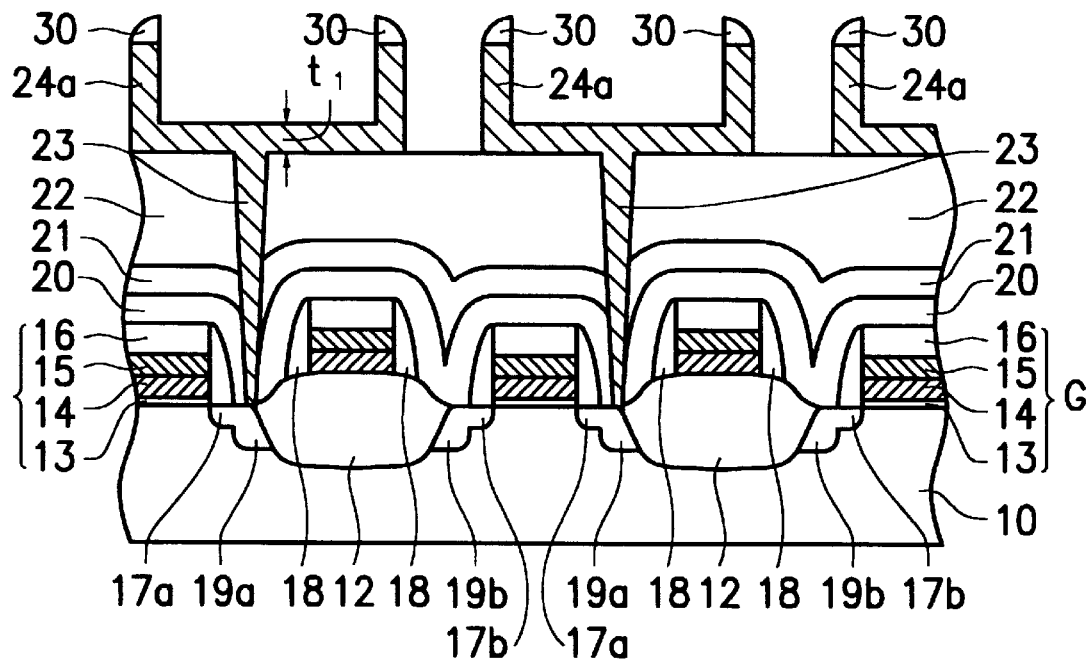
Figure 2C:
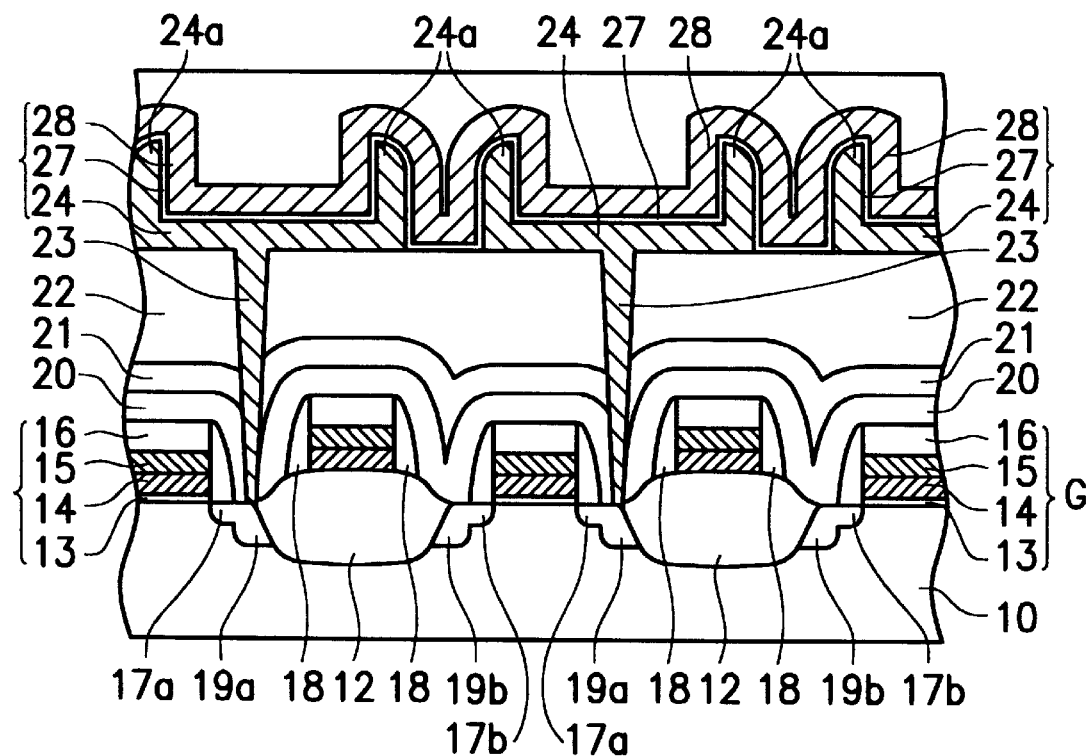
Figure 3A:
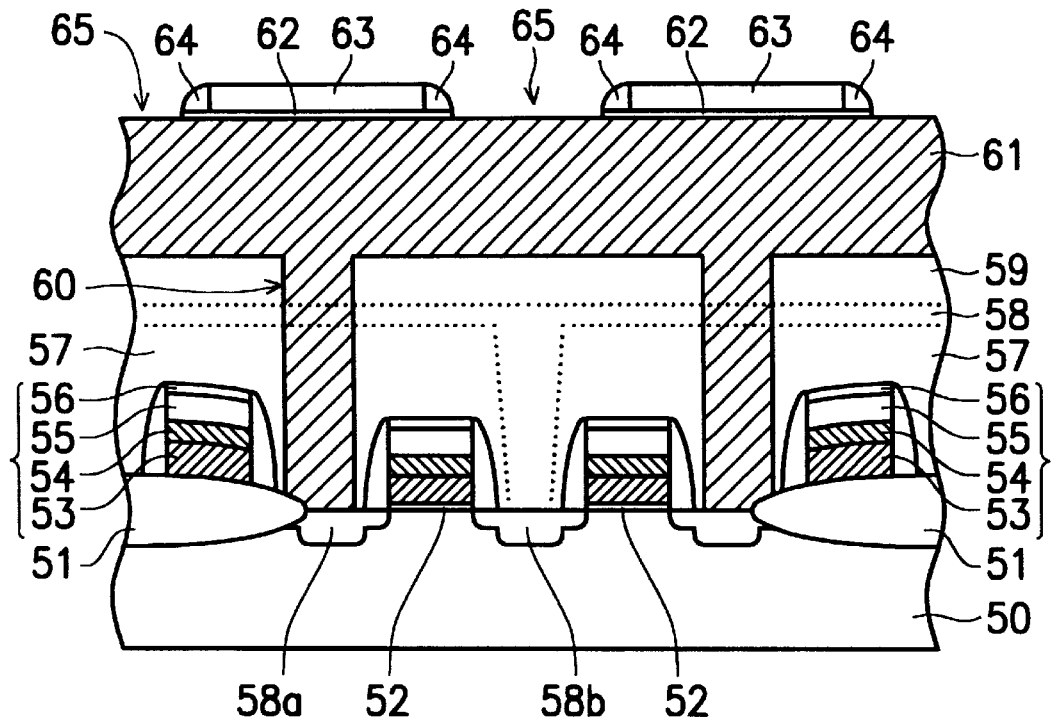
FIG. 3A, 3B, 3C, 3D and FIG. 3E are cross-sectional views illustrating the fabrication steps of a DRAM cell according to a first embodiment of the invention.

Referring to FIG. 3A, a transistor is formed over a semiconductor substrate. The transistor includes a gate, a source and a drain. The active region of the transistor can be defined by a field oxide layer 51, which is formed by, for example, the LOCOS method. The gate of the transistor is formed by successively depositing a gate oxide layer 52, a polysilicon layer 53, a tungsten silicide layer 54 a silicon dioxide layer 55 and an oxynitride layer 56, and then patterning these layers to a gate structure. The drain and source regions are formed by implanting ions in the semiconductor substrate. For example, using the gate structure G as a mask, impurities are implanted in the substrate to form lightly doped source/drain regions. Then a spacer is formed on the sidewall of the gate G by depositing and etching back a dielectric layer. Using the gate and the spacer as a mask, impurities, such as arsenate ($As^{75}$) of higher concentration are then implanted in the substrate 50 to form the source region 58a and the drain region 58b.

The transistor and the substrate 50 are then covered by at least one planar insulating layer. Moreover, corresponding conducting lines are arranged in the insulating layer. In the embodiment, a first BPSG layer 57 is deposited over the substrate 50 by the chemical vapor deposition (CVD) method. The first BPSG layer 57 is patterned by microlithography and etching to form a contact opening in which the drain region 58b is exposed. Then a conducting layer is deposited over the first BPSG layer 57 and fills in the contact opening to contact the drain region 58b. The conducting layer is defined as a bit line 58 of the memory cell by etching. Since the bit line 58 does not exist in the cross-sectional plane, it is illustrated by dashed line in the figure. Then a second BPSG layer 59 is deposited over the first BPSG layer 57 and the exposed bit line 58, and is patterned to form a contact opening 60 through the first BPSG layer 57 and the second BPSG layer 59 to expose the source region 58a of the transistor.

The contact opening 60 is then filled with a first conducting layer 61 that extends over the second BPSG layer 59. The first conducting layer 61 can be deposited by the CVD method to a thickness of about 3000 Å–20000 Å. Since the first conducting layer 61 electrically connects the source region 58a, its conductivity can be improved by implanting ions, such as arsenate ions, therein. The first conducting layer 61 is then successively covered by an etching stop layer 62 and a mask layer 63. The etching stop layer 62 which is, for example, a silicon dioxide layer is different from the first conducting layer 61. Moreover, the mask layer 63 can be a polysilicon or amorphous silicon layer. The mask layer 63 is patterned, by microlithography and etching, to have a plurality of openings 65, thereby exposing regions which separate various memory cells, that is, the regions between the contact openings 60. Alternatively, in order to simplify the process, the mask layer 63 can be a photoresist layer that defines the openings 65 directly after the microlithography step. As shown in FIG. 3A, a dielectric spacer 64 is formed on the sidewall of the mask layer 63. The dielectric spacer 64 is formed by depositing and etching back a dielectric layer, such as a silicon dioxide layer, a silicon nitride layer, or an oxynitride layer, over the mask layer 63. Then the mask layer 63 and the dielectric spacer 64 are both utilized as a mask to etch the exposed portions of the etching stop layer 62.

Figure 3B:
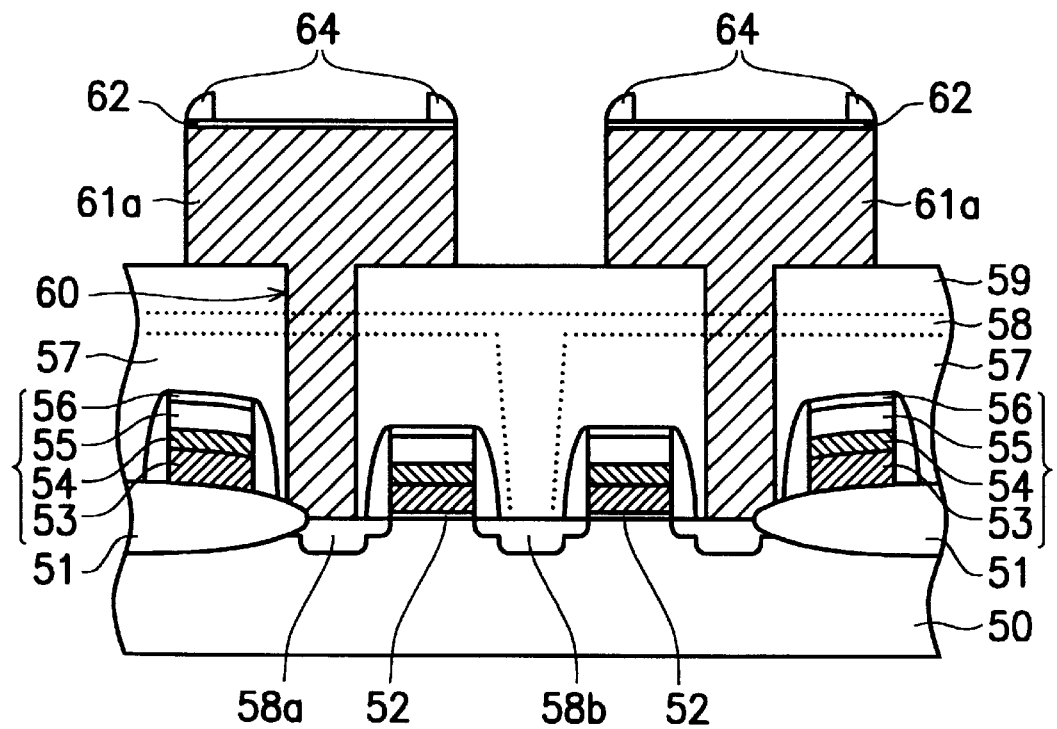

Referring to FIG. 3B, the dielectric spacer 64 is again utilized as a mask for reactive ion etching (RIE) anisotropically the mask layer 63 and the first conducting layer 61 to expose the etching stop layer 62 and the second BPSG layer 59, thereby forming the first conducting layer 61a of the figure, and defining a capacitor region. For if the mask layer 63 is a photoresist layer, the steps are: using the photoresist layer 63 and the dielectric spacer 64 as a mask for anisotropically etching the first conducting layer 61 to expose the second BPSG layer 64, then removing the photoresist layer 63. Since the first conducting layer 61a of the capacitor is protected by etching stop layer 62, its thickness does not change during the etching process.

Figure 3C:
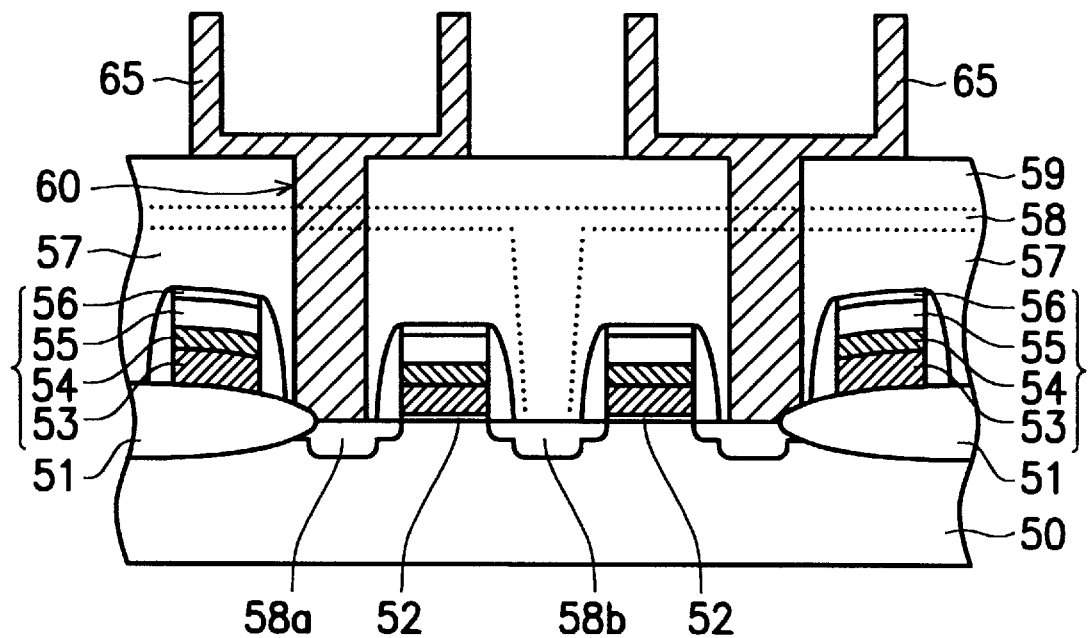

Referring to FIG. 3C, an etching step is carried out to remove uncovered portions of the etching stop layer 62, thereby exposing the first conducting layer 61a. The dielectric spacer 64 is then utilized as a mask for anisotropically etching the first conducting layer 61a to a predetermined thickness. Since the capacitor regions have been separated in the previous steps, the dilemma between over-etching to make sure the complete isolation of the storage node and controlling the remaining thickness of the storage node is not there at all, a storage electrode having a crown-type structure can be perfectly obtained. That is, the operating parameters of this etching step are enhanced. The dielectric spacer 64 and the etching stop layer 62 are then removed.

Figure 3D:
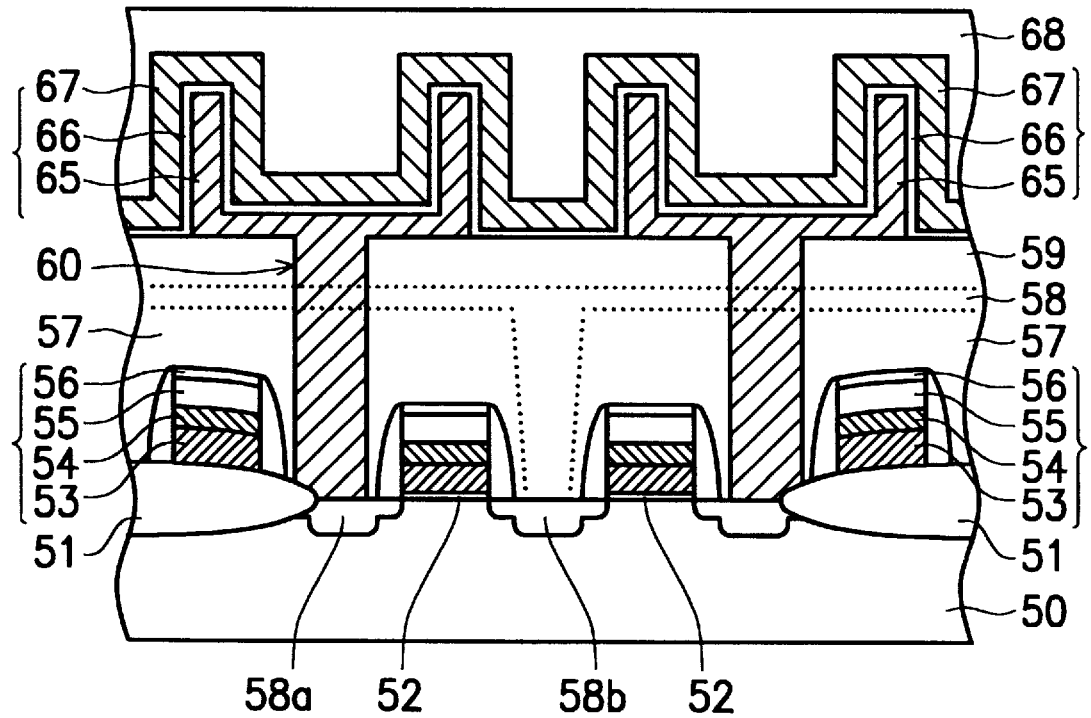

Referring to FIG. 3D, a dielectric layer 66 is formed over the exposed storage electrode 65. This dielectric layer 66 can be a silicon dioxide layer, a silicon nitride layer, an oxynitride layer, a Ta2O5 layer or a layer of ferroelectric material. The dielectric layer 66 is then covered by a second conducting layer which is formed by, for example, depositing polysilicon by the CVD method to a thickness of about 500–Å3000 Å, and then doped with ions to improving the conductivity. The second conducting layer is etched to be an opposite electrode 67 of the capacitor.

Figure 3E:
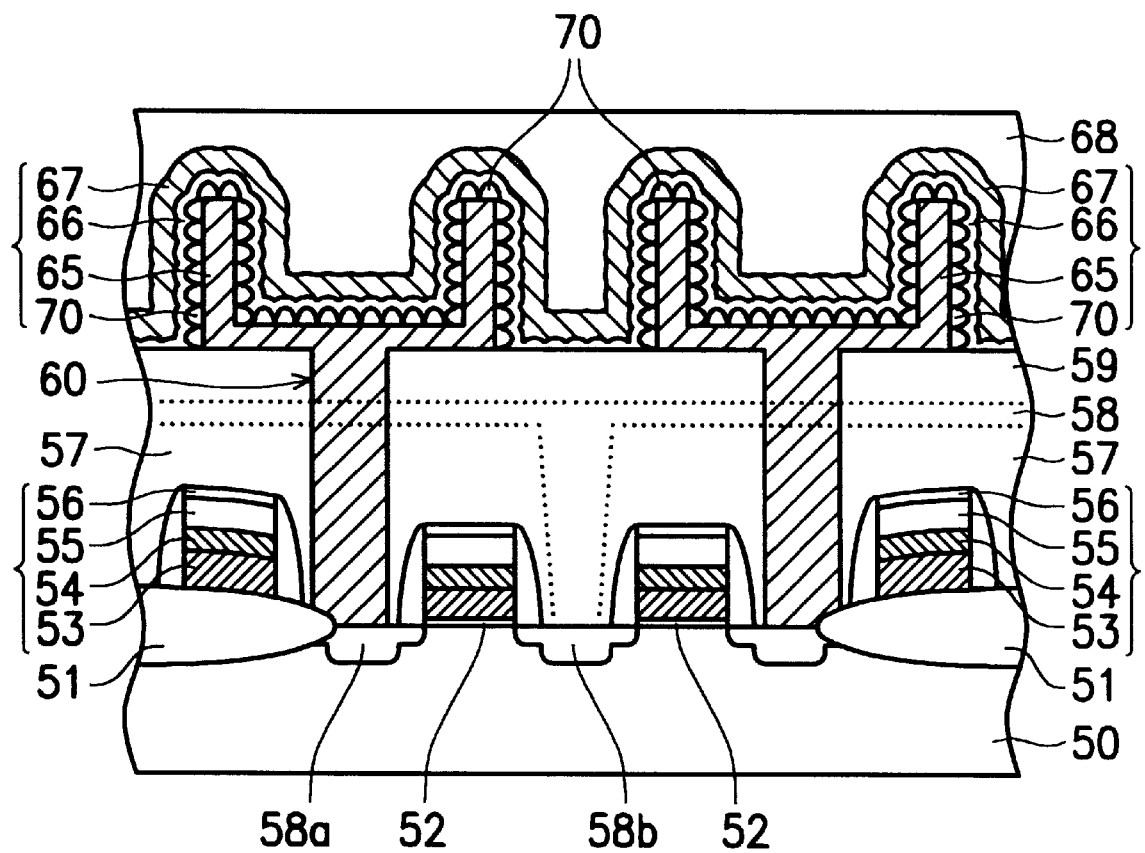

The aforementioned DRAM cell has the crown-type capacitor in which the capacitance is large enough for highly integrated applications. Moreover, the electrode area can be easily increased. For example, referring to FIG. 3E, a plurality of hemispherical silicon grains (HSG) or rugged polysilicon structures (by LPCVD method) can be formed over the exposed storage electrode 65, before the formation of the dielectric layer 66, thereby increasing the capacitance.

Embodiment 2

Figure 4A:
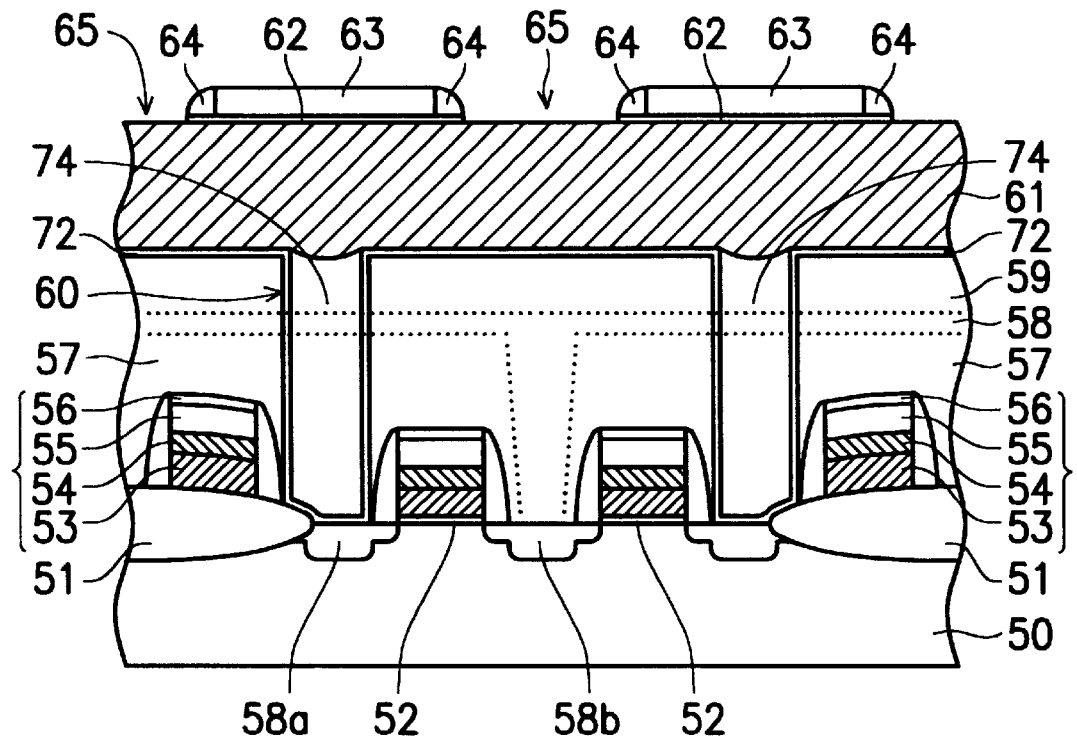
FIG. 4A and FIG. 4B are cross-sectional views illustrating the fabrication steps of a DRAM cell according to a second embodiment of the invention.

Referring to FIG. 4A, the steps described in the first embodiment are carried out to the formation of the contact opening 60. That is, a transistor, having a source region 58a, a drain region 58b and a gate including a gate oxide 52, a polysilicon layer 53, a tungsten silicide layer 54, an oxide layer 55 and an oxynitride layer 56, is formed over a semiconductor substrate 50 and is isolated by a field oxide layer 51. Then at least one planar layer is deposited over the substrate 50. For example, a first BPSG layer 57, a bit line 58 (shown by the dashed line) and a second BPSG layer 59 are successively formed over the substrate 50. These BPSG layers are patterned to form a contact opening 60 to expose the source region 58a of the transistor.

A Ti/TiN layer 72 having a thickness of about 500 Å–2000 Å is deposited to cover the sidewall and bottom of the contact opening 60, and extends over the second BPSG layer 59. Then a tungsten plug 74 is filled in the contact opening 60. The tungsten plug 74 and the exposed Ti/TiN layer are then covered with a first conducting layer 61. The first conducting layer 61 can be a polysilicon layer which is formed by the CVD method and has a thickness of about 3000 Å–20000 Å. The conductivity of the polysilicon layer can be improved by ion implantation, as it electrically connects the tungsten plug 74 and the Ti/TiN layer 72.

Then an etching stop layer 62 and a mask layer 63 are successively formed over the first conducting layer 61. The etching stop layer 62 is formed from material such as silicon dioxide, which is different from the first conducting line 61. The mask layer 63 can be a polysilicon or amorphous silicon layer. The mask layer 63 is patterned by microlithography and etching steps to form a plurality of openings 65, thereby exposing regions for separating different memory cells, that is, regions between the contact openings 60. Moreover, in order to simplify the process, the mask layer 63 can be a photoresist layer which defines the openings 65 directly after the microlithography step. A dielectric layer is then deposited and etched back to form dielectric spacer 64 on the sidewall of the mask layer 63. The dielectric spacer 64 is made of silicon dioxide, silicon nitride, or oxynitride. The mask layer 63 and the dielectric spacer 64 are both utilized as a mask for removing exposed portions of the etching stop layer 62, thereby forming the structure as shown in FIG. 4A.

The dielectric spacer 64 is again utilized as a mask for anisotropically etching the mask layer 63 and the first conducting layer 61 to expose the etching stop layer 62 and the Ti/TiN layer 72, thereby defining a capacitor region. The reactive ion etching (RIE) method can be carried out. For if the mask layer 63 is a photoresist layer, the photoresist layer and the dielectric spacer are both utilized as a mask in the etching step for defining the capacitor region, and then the photoresist layer is removed.

Figure 4B:
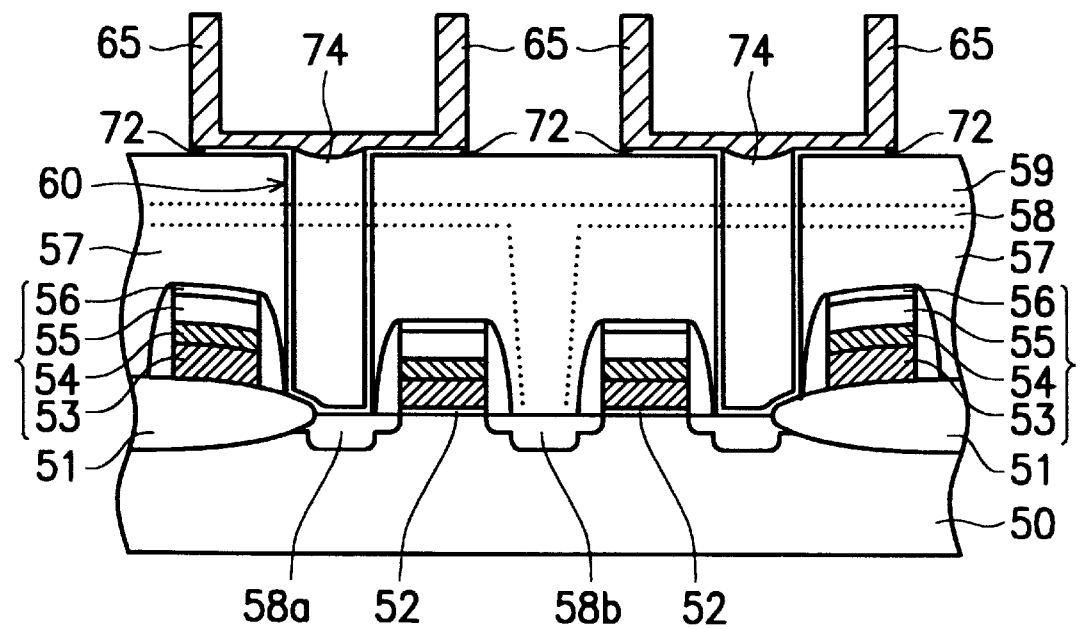

Referring to FIG. 4B, the uncovered Ti/TiN layer 72 and uncovered etching stop layer 62 in the capacitor region are both removed through an etching step. Then the dielectric spacer 64 is utilized as a mask for anisotropically etching the first conducting layer 61 to a predetermined depth, thereby forming a crown-type structure. Therefore, the tungsten plug 74, Ti/TiN layer 72 and the first conducting layer 61 constitute the crown-type storage capacitor 65. Similarly, since the capacitor regions have been separated in the previous process steps, the first conducting layer need not to be over etched for forming the crown-type structure, thereby retaining the thickness and providing broader operating parameters. The dielectric spacer 64 and the etching stop layer 62 are then removed to produce the structure of FIG. 4B. Since the proceeding steps are the same as those of the first embodiment, their descriptions are omitted.

Embodiment 3

Figure 5A:
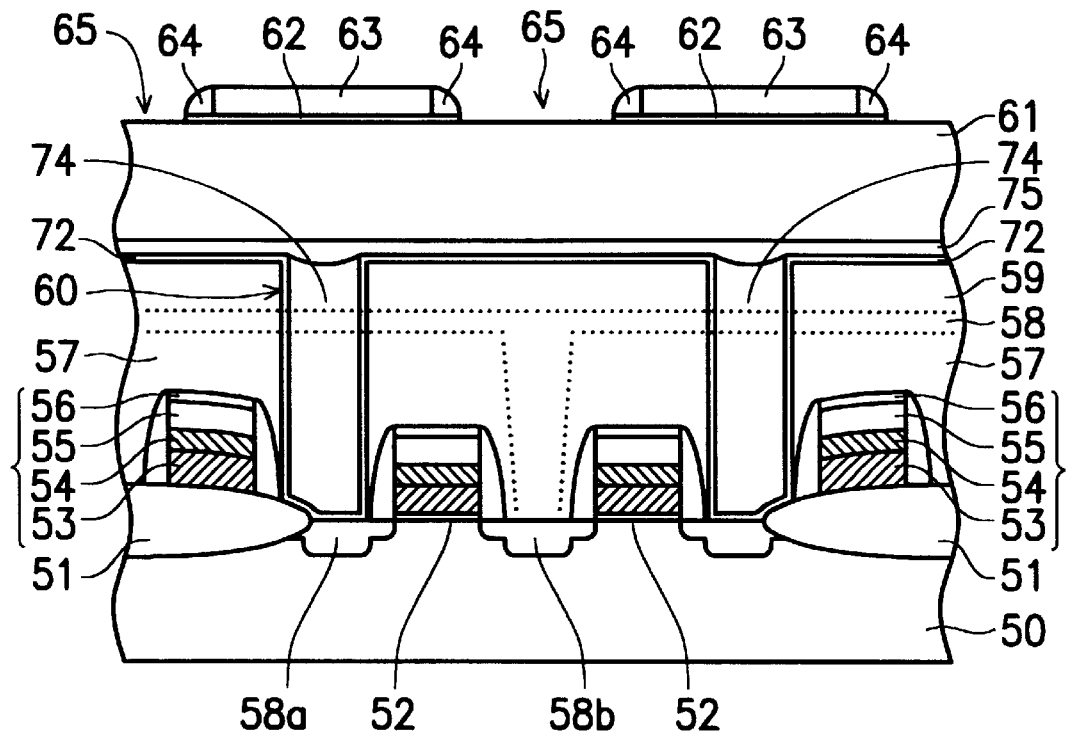
FIG. 5A and FIG. 5B are cross-sectional views illustrating the fabrication steps of a DRAM cell according to a third embodiment of the invention.

Referring to FIG. 5A, the steps described in the first embodiment are carried out through the formation of the contact opening 60. That is, a transistor, having a source region 58a, a drain region 58b and a gate including a gate oxide 52, a polysilicon layer 53, a tungsten silicide layer 54, an oxide layer 55 and an oxynitride layer 56, is formed over a semiconductor substrate 50 and is isolated by a field oxide layer 51. Then at least one planar layer is deposited over the substrate 50. For example, a first BPSG layer 57, a bit line 58 (shown by dashed line) and a second BPSG layer 59 are successively formed over the substrate 50. These BPSG layers are patterned to form a contact opening 60 to expose the source region 58a of the transistor.

Then a first Ti/TiN layer 72 having a thickness of about 500 Å–2000 Å is deposited on the sidewall and bottom of the contact opening 60 and extends over the second BPSG layer 59. A tungsten plug 74 is filled in the contact opening 60. The tungsten plug 74 and the first Ti/TiN layer 72 are then covered by a second Ti/TiN layer 75 which has a thickness of about 800 Å–2500 Å. A first conducting layer 61 is then deposited over the second Ti/TiN layer 75 to electrically connect the source region 58a through the tungsten plug 74. The first conducting layer 61 can be a polysilicon layer which is formed by, for example, the CVD method, to a thickness of about 3000 Å–20000 Å. The conductivity of the polysilicon conducting line 61 can be improved by implanting ions therein.

The first conducting layer 61 is covered by an etching stop layer 62 and a mask layer 63. The etching stop layer 62 is made of material different from that of the first conducting layer 61. For example, the etching stop layer 62 can be a silicon dioxide layer. The mask layer 63 can be a polysilicon layer or an amorphous silicon layer. The mask layer 63 is then patterned by microlithography and etching to form a plurality of openings 65, thereby exposing regions for separating different memory cells, that is, regions between the contact openings 60. A dielectric layer is deposited and etched back to form a dielectric spacer 64 on the sidewall of the mask layer 64. The dielectric layer can be a silicon dioxide, silicon nitride, or oxynitride layer. The mask layer 63 and the dielectric spacer 64 are then utilized as a mask for removing exposed portions of the etching stop layer 62, thereby producing the structure of FIG. 5A.

Figure 5B:
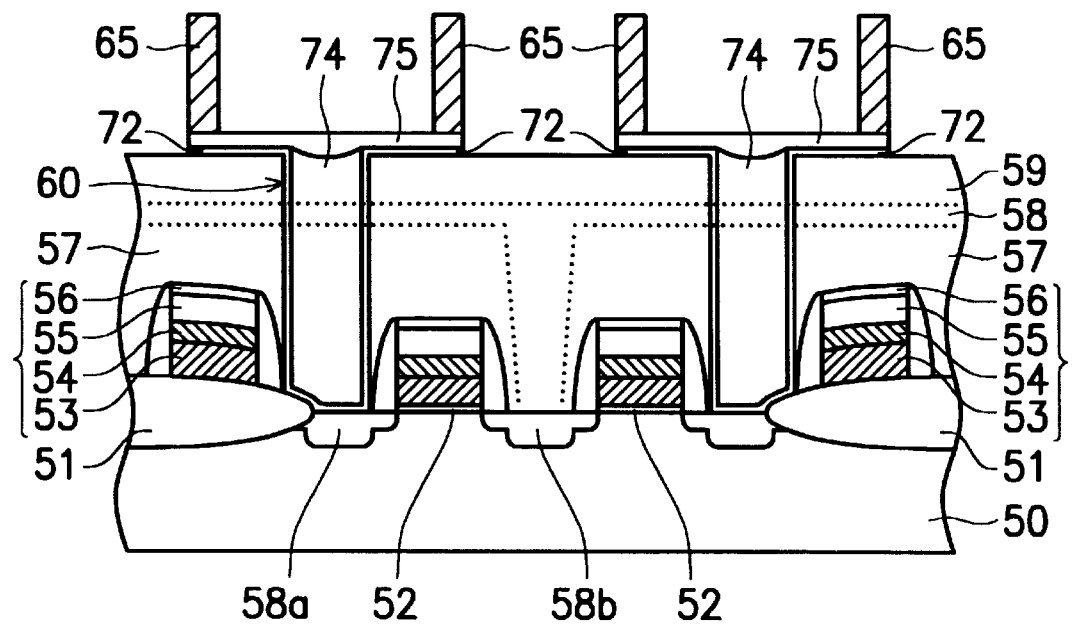

The dielectric spacer 64 is again utilized as a mask for anisotropically etching the mask layer 63 and the first conducting layer 61 to expose the etching stop layer 62 and the second Ti/TiN layer 75. This etching step can be carried out by the reactive ion etching method. As the capacitor region is defined, referring to FIG. 5B, the uncovered portions of the first and second Ti/TiN layers 72 and 75, and those of the etching stop layer 62 in the capacitor region, are removed.

The dielectric spacer 64 is utilized as a mask for anisotropically etching the first conducting layer 61 to expose the second Ti/TiN layer 75, thereby forming a crown-type structure. Therefore, the tungsten plug 74, the first and the second Ti/TiN layer 72 and 75, and the first conducting layer 61 constitute the crown-type storage capacitor 65. Similarly, since the capacitor regions have been separated in the previous process steps, the first conducting layer need not to be over etched for forming the crown-type structure, thereby retaining the thickness and providing broader operating parameters. The dielectric spacer 64 and the etching stop layer 62 are then removed to produce the structure of FIG. 4B. Since the proceeding steps are the same as those of the first embodiment, their descriptions are omitted.

The aforementioned embodiments of the invention can be applied independently or combined together to fabricate various storage electrode structures. Moreover, even though the drain region of the transistor is a diffusion region, it can be another structure, such as a trench-type drain structure. These modifications all fall within the scope of the invention, as is known to those skilled in the art.

What is claimed is:

1. A method for fabricating a DRAM cell with a crown-type capacitor over a semiconductor substrate, comprising the steps of:
   (a) forming a transistor including a gate, a drain and a source over the semiconductor substrate;
   (b) forming an insulating layer over the transistor;
   (c) selectively etching the insulating layer to form a contact opening in which either the source or the drain of the transistor is exposed as a contact region;
   (d) forming a first conducting layer over the insulating layer and filling into the contact opening to electrically connect the contact region;
   (e) successively forming an etching stop layer and a mask layer over the first conducting layer, wherein the etching stop layer and the first conducting layer consist of different materials;
   (f) patterning the mask layer to form a plurality of openings in which regions for separating different memory cells are exposed;
   (g) forming a dielectric spacer on the sidewall of the mask layer, and removing exposed portions of the etching stop layer;
   (h) anisotropically etching the mask layer and the first conducting layer by using the dielectric spacer as a mask, to expose, respectively, the etching stop layer and the insulating layer, for defining a capacitor region;
   (i) removing the uncovered etching stop layer to expose the first conducting layer;
   (j) anisotropically etching the first conducting layer to a predetermined depth by using the dielectric spacer as a mask, thereby forming a crown-type storage electrode;
   (k) removing the dielectric spacer and the etching stop layer;
   (l) forming a dielectric layer over exposed portions of the storage electrode; and
   (m) forming a second conducting layer as an opposite electrode over the dielectric layer.

2. The method as claimed in claim 1, wherein the insulating layer includes at least one BPSG layer in which a bit line is formed.

3. The method as claimed in claim 1, wherein the first conducting layer is a polysilicon layer which has a thickness of about 3000 Å–20000 Å.

4. The method as claimed in claim 1, wherein the mask layer is a polysilicon layer or an amorphous silicon layer.

5. The method as claimed in claim 1, wherein the dielectric spacer includes a silicon dioxide layer, a silicon nitride layer or an oxynitride layer.

6. The method as claimed in claim 1 further comprising the step of forming a plurality of hemispherical silicon grains or rugged polysilicon structures over the exposed storage electrode before the step (1).

7. The method as claimed in claim 1, wherein the material of the dielectric layer is selected from the group consisting of silicon dioxide, silicon nitride, oxynitride, $Ta_2O_5$, and ferroelectric material.

8. The method as claimed in claim 1, wherein the second conducting layer is a polysilicon layer.

9. The method as claimed in claim 1, wherein the mask layer is a photoresist layer.

10. A method for fabricating a DRAM cell with a crown-type capacitor over a semiconductor substrate, comprising the steps of:
    (a) forming a transistor including a gate, a drain and a source over the semiconductor substrate;
    (b) forming an insulating layer over the transistor;
    (c) selectively etching the insulating layer to form a contact opening in which either the source or the drain of the transistor is exposed as a contact region;
    (d) forming a Ti/TiN layer covering the sidewall and bottom of the contact opening, and extending over the insulating layer;
    (e) forming a tungsten plug in the contact opening;
    (f) forming a first conducting layer over the exposed Ti/TiN surface, and electrically connecting the tungsten plug;
    (g) successively forming an etching stop layer and a mask layer over the first conducting layer, wherein the etching stop layer and the first conducting layer consist of different materials;
    (h) patterning the mask layer to form a plurality of openings in which regions for separating different memory cells are exposed;
    (i) forming a dielectric spacer on the sidewall of the mask layer, and removing exposed portions of the etching stop layer;
    (j) anisotropically etching the mask layer and the first conducting layer by using the dielectric spacer as a mask, to expose, respectively, the etching stop layer and the Ti/TiN layer, for defining a capacitor region;
    (k) removing uncovered Ti/TiN layer and uncovered etching stop layer to expose the first conducting layer;
    (l) anisotropically etching the first conducting layer to a predetermined depth by using the dielectric spacer as a mask, thereby forming a crown-type storage electrode including the tungsten plug, the Ti/TiN layer and the first conducting layer;
    (m) removing the dielectric spacer and the etching stop layer;
    (n) forming a dielectric layer over exposed portions of the storage electrode; and
    (o) forming a second conducting layer as an opposite electrode over the dielectric layer.

11. The method as claimed in claim 10, wherein the insulating layer is a BPSG layer in which a bit line is formed.

12. The method as claimed in claim 10, wherein the first conducting layer is a polysilicon layer, and the second conducting layer is a polysilicon layer.

13. The method as claimed in claim 10, wherein the mask layer is a polysilicon layer or an amorphous silicon layer.

14. The method as claimed in claim 10, wherein the dielectric spacer includes a silicon dioxide layer, a silicon nitride layer, or an oxynitride layer.

15. The method as claimed in claim 10, wherein the material of the dielectric layer is selected from the group consisting of silicon dioxide, silicon nitride, oxynitride, $Ta_2O_5$, and ferroelectric material.

16. A method for fabricating a DRAM cell with a crown-type capacitor over a semiconductor substrate, comprising the steps of:

(a) forming a transistor including a gate, a drain and a source over the semiconductor substrate;

(b) forming an insulating layer over the transistor;

(c) selectively etching the insulating layer to form a contact opening in which either the source or the drain of the transistor is exposed as a contact region;

(d) forming a first Ti/TiN layer covering the sidewall and bottom of the contact opening, and extending over the insulating layer;

(e) forming a tungsten plug in the contact opening;

(f) forming a second Ti/TiN layer covering the tungsten plug and the first Ti/TiN layer, wherein the second Ti/TiN layer has a thickness greater than that of the first Ti/TiN layer;

(g) forming a first conducting layer over the exposed second Ti/TiN surface, and electrically connecting the tungsten plug;

(h) successively forming an etching stop layer and a mask layer over the first conducting layer, wherein the etching stop layer and the first conducting layer consist of different materials;

(i) patterning the mask layer to form a plurality of openings in which regions for separating different memory cells are exposed;

(j) forming a dielectric spacer on the sidewall of the mask layer, and removing exposed portions of the etching stop layer;

(k) anisotropically etching the mask layer and the first conducting layer by using the dielectric spacer as a mask, to expose, respectively, the etching stop layer and the Ti/TiN layer, for defining a capacitor region;

(l) removing uncovered first and second Ti/TiN layers and the uncovered etching stop layer to expose the first conducting layer;

(m) anisotropically etching the first conducting layer to the second Ti/TiN layer by using the dielectric spacer as a mask, thereby forming a crown-type storage electrode including the tungsten plug, the first Ti/TiN layer, the second Ti/TiN layer and the first conducting layer;

(n) removing the dielectric spacer and the etching stop layer;

(o) forming a dielectric layer over the exposed portions of the storage electrode; and (p) forming a second conducting layer as an opposite electrode over the dielectric layer.

17. The method as claimed in claim 16, wherein the insulating layer is a BPSG layer in which a bit line is formed.

18. The method as claimed in claim 16, wherein the first conducting layer is a polysilicon layer, and the second conducting layer is a polysilicon layer.

19. The method as claimed in claim 16, wherein the mask layer is a polysilicon layer or an amorphous silicon layer.

20. The method as claimed in claim 16, wherein the dielectric spacer includes a silicon dioxide layer, a silicon nitride layer, or an oxynitride layer.

21. The method as claimed in claim 16, wherein the material of the dielectric layer is selected from the group consisting of silicon dioxide, silicon nitride, oxynitride, $Ta_2O_5$, and ferroelectric material.

* * * * *